United States Patent [19]

Sih

[11] 4,254,041
[45] Mar. 3, 1981

[54] 19-HYDROXY-5-HYDROXY-PGI COMPOUNDS

[75] Inventor: John C. Sih, Portage, Mich.

[73] Assignee: The Upjohn Company, Kalamazoo, Mich.

[21] Appl. No.: 126,477

[22] Filed: Mar. 3, 1980

Related U.S. Application Data

[62] Division of Ser. No. 54,811, Jul. 5, 1979, Pat. No. 4,225,508.

[51] Int. Cl.³ .................................... C07D 307/935
[52] U.S. Cl. ..................... 260/346.22; 260/346.73; 542/421; 542/422; 542/416; 542/426; 548/252; 548/253

[58] Field of Search .................. 260/346.22, 346.73; 542/416, 421, 422, 426; 548/252, 253

[56] References Cited

PUBLICATIONS

Johnsen et al., Prostaglandins 12, 916–928, (1976).

*Primary Examiner*—Henry R. Jiles
*Assistant Examiner*—Bernard Dentz
*Attorney, Agent, or Firm*—Robert A. Armitage

[57] ABSTRACT

The present invention provides novel 19-hydroxy-5-hydroxy-PGI compounds which are useful for pharmacological purposes, e.g., anti-asthmatic indications.

5 Claims, No Drawings

19-HYDROXY-5-HYDROXY-PGI COMPOUNDS

CROSS REFERENCE TO RELATED APPLICATION

The present invention is a divisional application of United States Ser. No. 054,811, filed July 5, 1979, now U.S. Pat. No. 4,225,508.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-5-hydroxy-PGI compounds. The novel prostacyclin analogs are useful for pharmacological purposes, e.g., as anti-asthmatic agents. The preparation and use of these compounds is incorporated here by reference from U.S. Pat. No. 4,225,508.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of $PGI_2$, see R. A. Johnson, et al., Prostaglandins 15, 737–740 (1978).

SUMMARY OF THE INVENTION

The present invention particularly provides a prostacyclin-type compound of the formula

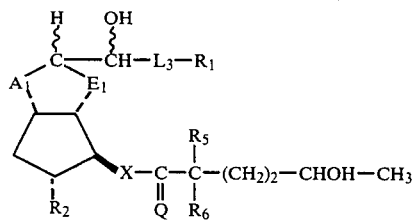

wherein $A_1$ is —O— (oxa) and $E_1$ is —$CH_2$—;
wherein $L_3$ is
 (1) —$(CH_2)_n$—, wherein n is one to 5, inclusive,
 (2) —$(CH_2)_p$—$CF_2$—, wherein p is 2, 3, or 4; or
 (3) —$CH_2$—CH=CH—;
wherein Q is oxo, α-H:β-H, α-OH:β-$R_4$, or α-$R_4$:β-OH,
wherein $R_1$ is
 (1) —$COOR_3$,
 (2) —$CH_2OH$,
 (3) —$CH_2N(R_7)(R_8)$,
 (4) —CO—$N(R_7)(R_8)$,
 (5) —CO—NH—$SO_2$—$R_{15}$, or
 (6) tetrazolyl,
wherein $R_3$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive;
 (g) —(p-Ph)—CO—$CH_3$,
 (h) —(p—Ph)—NH—CO—(p-Ph)-NH-CO-$CH_3$,
 (i) —(p—Ph)—NH—CO—(Ph),
 (j) —(p—Ph)—NH—CO—$CH_3$,
 (k) —(p—Ph)—NH—CO—$NH_2$,
 (l) —(p—Ph)—CH=N—NH—CO—$NH_2$,
 (m) β-naphthyl,
 (n) —$CH_2$—CO—$R_{16}$,
wherein —(p-Ph)— is para-phenylene and —(Ph) is phenyl;
wherein $R_{16}$ is phenyl, p-bromophenyl, p-biphenylyl, p-nitrophenyl, p-benzamidophenyl, or 2-naphthyl, or
 (o) a pharmacologically acceptable cation; wherein $R_7$ and $R_8$ are hydrogen, alkyl of one to 12 carbon atoms, inclusive, benzyl, or phenyl, being the same or different, and wherein $R_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein $R_2$ is hydrogen, hydroxyl, or hydroxymethyl,
wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro, and
wherein X is
 (1) trans—CH=CH—,
 (2) cis—CH=CH—,
 (3) —C≡C—, or
 (4) —$CH_2CH_2$—.

DESCRIPTION OF THE PREFERRED EMBODIMENTS

The present invention particularly relates to the following compounds:
2-Decarboxy-2-hydroxymethyl-9-deoxy-6ξ,9α-epoxy-5ξ,19-dihydroxy-$PGF_1$, and
2-Decarboxy-2-hydroxymethyl-9-deoxy-6ξ,9α-epoxy-5ξ,19-dihydroxy-16,16-difluoro-$PGF_1$.

I claim:
1. A prostacyclin-type compound of the formula

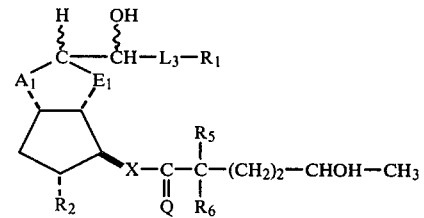

wherein $A_1$ is —O— (oxa) and $E_1$ is —$CH_2$—;
wherein $L_3$ is
 (1) —$(CH_2)_n$—, wherein n is one to 5, inclusive,
 (2) —$(CH_2)_p$—$CF_2$—, wherein p is 2, 3, or 4; or
 (3) —$CH_2$—CH=CH—;
wherein Q is oxo, α-H:β-H, α-OH:β-$R_4$, or α-$R_4$:β-OH,
wherein $R_1$ is
 (1) —$COOR_3$,
 (2) —$CH_2OH$,
 (3) —$CH_2N(R_7)(R_8)$,
 (4) —CO—$N(R_7)(R_8)$, (5) —CO—NH—SO$_2$—R$_{15}$, or
(6) tetrazolyl,
wherein R$_3$ is
  (a) hydrogen,
  (b) alkyl of one to 12 carbon atoms, inclusive,
  (c) cycloalkyl of 3 to 10 carbon atoms, inclusive,
  (d) aralkyl of 7 to 12 carbon atoms, inclusive,
  (e) phenyl,
  (f) phenyl substituted with one, 2, or 3 chloro or alkyl groups
of one to 3 carbon atoms, inclusive;
  (g) —(p-Ph)—CO—CH$_3$,
  (h) —(p-Ph)—NH—CO—(p—Ph)—NH—CO—CH$_3$,
  (i) —(p—Ph)—NH—CO—(Ph),
  (j) —(p—Ph)—NH—CO—CH$_3$,
  (k) —(p-Ph)—NH—CO—NH$_2$,
  (l) —(p—Ph)—CH=N—NH—CO—NH$_2$,
  (m) β-naphthyl,
  (n) —CH$_2$—CO—R$_{16}$,
wherein (p—Ph)— is para-phenylene and —(Ph) is phenyl;
wherein R$_{16}$ is phenyl, p-bromophenyl, p-biphenylyl, p-nitrophenyl, p-benzamidophenyl, or 2-naphthyl, or
  (o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and
wherein X is
  (1) trans—CH=CH—,
  (2) cis—CH=CH—,
  (3) —C≡C—, or
  (4) —CH$_2$CH$_2$—.

2. A compound according to claim 1, wherein R$_1$ is —CH$_2$OH.

3. A compound according to claim 2, wherein L$_3$ is —(CH$_2$)$_3$, Q is α-OH:β-H, R$_2$ is hydroxyl, and X is trans—CH=CH—.

4. 2-Decarboxy-2-hydroxymethyl-9-deoxy-6ξ,9α-epoxy-5ξ,19-dihydroxy-PGF$_1$, a compound according to claim 3.

5. 2-Decarboxy-2-hydroxymethyl-9-deoxy-6ξ,9α-epoxy-5ξ,19-dihydroxy-16,16-difluoro-PGF$_1$, a compound according to claim 3.

* * * * *